United States Patent [19]

Kohno et al.

[11] 4,212,062
[45] Jul. 8, 1980

[54] TOMOGRAPHIC IMAGING SYSTEM

[75] Inventors: Hideki Kohno, Tokyo; Hidemi Shiono, Akikawa; Chitose Nakaya, Hachioji; Kensuke Sekihara, Sakamachi; Teruichi Tomura, Kunitachi; Shinji Yamamoto; Takayuki Hayakawa, both of Hachioji; Isao Horiba; Shigenobu Yanaka, both of Kashiwa, all of Japan

[73] Assignee: Hitachi Medical Corporation, Japan

[21] Appl. No.: 919,627

[22] Filed: Jun. 27, 1978

[30] Foreign Application Priority Data

Oct. 21, 1977 [JP] Japan .................... 52-126490

[51] Int. Cl.$^2$ ............ G01N 23/04; G06F 15/34
[52] U.S. Cl. ...................... 364/414; 250/445 R
[58] Field of Search ............. 364/414; 250/445 R, 250/445 T

[56] References Cited

U.S. PATENT DOCUMENTS

| 4,032,761 | 6/1977 | Mayo et al. | 250/445 T X |
| 4,066,903 | 1/1978 | Lemay | 250/455 T X |
| 4,128,877 | 12/1978 | Katz | 364/414 |

Primary Examiner—Jerry Smith
Attorney, Agent, or Firm—Craig and Antonelli

[57] ABSTRACT

A tomographic imaging system is disclosed in which the quantity of absorption or transmittance of a transmissive radiation by or through a certain tomographic cross-section of an object under consideration is detected and the distribution of radiation absorption or transmittance in the cross-section is reconstructed through a convolution operation. A weighting function used in the convolution operation is prepared with a predetermined one of its positive orders the value of which is an integration of the weighting function from the predetermined positive order to positive infinity and a predetermined one of its negative orders the value of which is in integration of the weighting function from the predetermined negative order to negative infinity.

3 Claims, 12 Drawing Figures

TOMOGRAPHIC IMAGING SYSTEM

This invention relates to a tomographic imaging system in which the distribution of absorption or transmittance of a transmissive radiation by or through a certain tomographic cross-section of an object under consideration is accurately reconstructed.

A method of reconstructing the distribution of X-ray absorption by or transmittance through a tomographic cross-section of a three-dimensional object is disclosed in detail by G. N. Ramachandran and A. V. Lakshminarayanan, "Three-Dimensional reconstruction from Radiographs and Electron micrographs: Application of convolutions instead of Fourier Transforms" Proceedings of the National Academy U.S.A., Vol. 68, No. 9, September 1971. Since the disclosed method requires an integration over an infinite region, the application of that method to an actual system is not practical. If the region to be integrated is narrowed, the accuracy of the reconstructed absorption or transmittance distribution is degrated depending upon the size of the object under consideration or when the object is surrounded by X-ray compensating substance or water.

An object of this invention is to provide a tomographic imaging system in which an integration over an infinite region is substantially realized by an integration over a finite region.

According to one aspect of this invention, there is provided a tomographic imaging system comprising, irradiating means for irradiating a cross-section of an object under consideration with radiation rays from plural directions, detector means for detecting the radiation rays transmitted through the cross-section of said object to produce an output signal, and an image reconstructing section for performing a convolution integral operation on the output signal of said detector means by means of a predetermined weighting function to reconstruct a three-dimensional image of the cross-section of said object, said weighting function being provided with a predetermined one of its positive orders the value of which is an integration of said weighting function from the predetermined positive order to positive infinity and a predetermined one of its negative orders corresponding to said predetermined positive order, the value of which predetermined negative order is an integration of said weighting function from the predetermined negative order to negative infinity.

According to another aspect of this invention, there is provided a tomographic imaging system comprising irradiating means for irradiating a cross-section of an object under consideration with radiation rays from plural directions, detector means for detecting the radiation rays transmitted through the cross-section of said object to produce an output signal, and an image reconstructing section for performing a convolution integral operation on the output signal of said detector means by means of a predetermined weighting function to reconstruct a three-dimensional image of the cross-section of said object, said image reconstruction section including a first means for generating a first weighting function, a second means for generating second and third weighting functions, said second function being integrations of said first weighting function from predetermined positive orders of said first weighting function to positive infinity and said third weighting function being integrations of said first weighting function from predetermined negative orders of said first weighting function to negative infinity, a third means for producing the product of the output from said detector means and the output from said first means, a fourth means for producing the sum of the outputs from said third means, fifth and sixth means for producing the product of the output from said detector means and said second weighting function and the product of the output from said detector means and said third weighting function, a seventh means for producing the sum of the output from said fifth means and the output from said sixth means, and an eighth means for producing the sum of the output from said fourth means and the output from said seventh means.

The above object and features of this invention will become apparent from the following description taken in conjunction with the accompanying drawings, in which.

Figure 1:
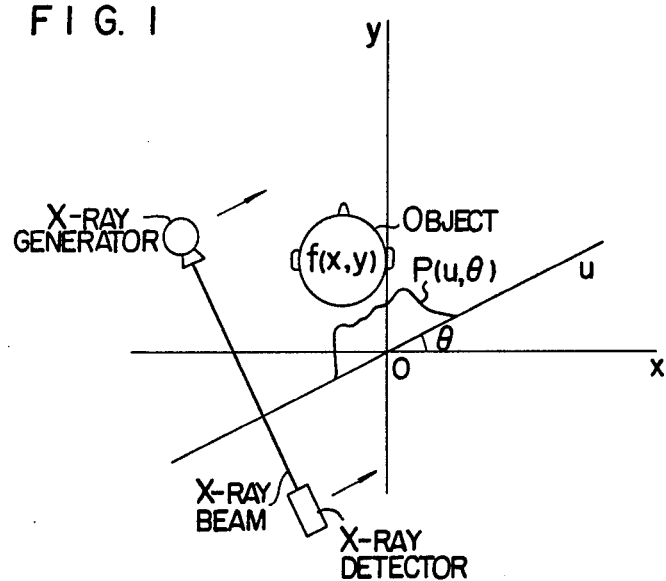
FIG. 1 is a view for explaining the principle of tomographic-image reconstruction.

Referring to FIG. 1, an X-ray generator for generating collimated X-ray beams and an X-ray detector for detecting X-rays transmitted through an object under consideration are moved in parallel with each other along an axis u which is inclined by an angle $\theta$ with respect to any given axis x. The principle of tomographic-image reconstruction using a convolution operation is based on the fact that between a transmittance data signal P (u, $\theta$) derived from the X-ray detector and the X-ray absorption distribution f (x, y) in the cross-section of the object is satisfied the following relationship:

$$f(x,y) = \frac{1}{2\pi} \int_0^\pi d\theta \int_{-\infty}^\infty \hat{P}(\omega,\theta) |\omega| \exp(j\omega u) \, d\omega \quad (1)$$

$$\hat{P}(\omega,\theta) = \int_{-\infty}^\infty P(u,\theta) \exp(-j\omega u) \, d\omega$$

The equation (1) can be readily written in a convolution form as follows:

$$f(x,y) = \int_0^\pi d\theta \int_{-\infty}^\infty P(u - u',\theta)\phi(u') \, du' \quad (2)$$

The weighting function $\phi(u)$ appearing in the equation (2) may be mathematically represented as follows:

$$\phi(u) = \int_{-\infty}^\infty |\omega| \exp(j\omega u) \, du \quad (3)$$

Another forms or modifications of the function $\phi(u)$ are well known. Whichever form of the function $\phi(u)$ is used, the calculation according to the equation (2) requires an integration over an infinite region. The calculation according to the equation (2) will be considered in connection with two cases.

Figure 2A:
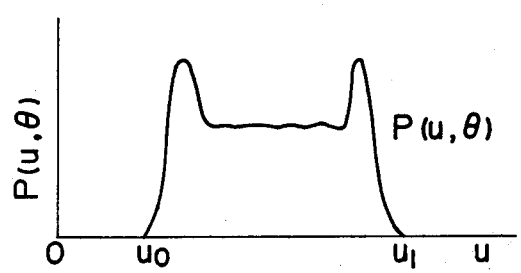
FIGS. 2A to 2C and FIGS. 3A to 3C are graphs showing the integration ranges of convolution operation.
Figure 2B:
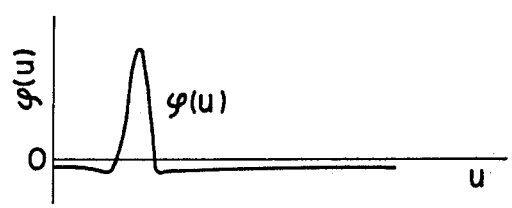
Figure 2C:

In such a first case as shown in FIGS. 2A to 2C in which P(u, θ) is not zero in a range of $u_o \leq u \leq u_1$ and is zero in ranges of $u < u_o$ and $u > u_1$, the equation (2) may be transformed into the following equation:

$$f(x,y) = \int_o^\pi d\theta \int_{u_o}^{u_1} P(u - u',\theta)\phi(u') du' \quad (3)$$

Accordingly, when the zero order of φ(u) defined at the center of φ(u) having usually a symmetrical shape is positioned at a point of $u = u_o$ (FIG. 2B) or $u = u_1$ (FIG. 2C), it is enough if φ(u) is defined within a range of P(u, θ)≠0. Assuming that P(u, θ) has been sampled at M points between $u = u_o$ and $u = u_1$, (2M−1) values of the weighting function φ(u) are enough.

Figure 3A:
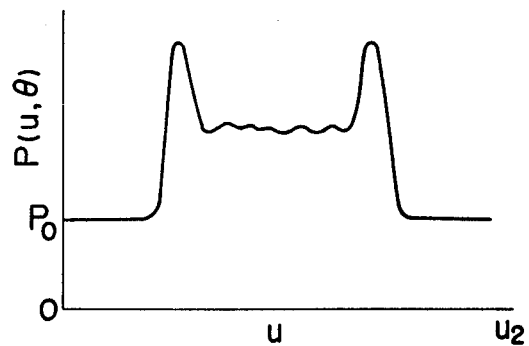
Figure 3B:
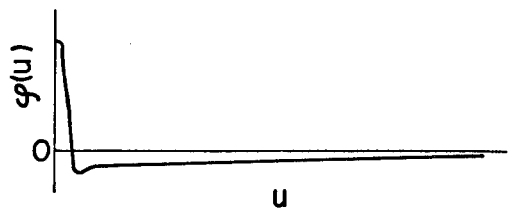
Figure 3C:
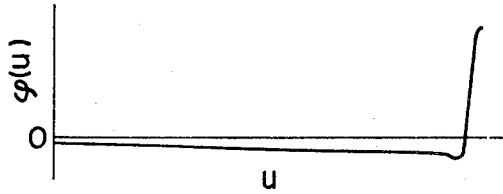

In such a second case as shown in FIGS. 3A to 3C in which P(u, θ) is not zero at any value of u, e.g. when the outer periphery of the cross-section of an object under consideration whose image is to be reproduced is surrounded by a uniform atmosphere such as water or plastics where the quantity of X-ray absorption is not zero, the equation (2) may be transformed into the following equation:

$$f(x,y) = \int_o^\pi d\theta \int_{-u_2}^{u_2} P(u - u',\theta)\phi(u') du' \quad (4)$$

It is possible to perform the calculation according to the equation (4) if it is assumed that P(u, θ) has a constant value $P_o$ at a range except $u = 0 \sim u_2$. However, even if the calculation of the equation (4) has been performed in such a manner, an accurate distribution f(x, y) cannot be obtained. The reason is that the integration E in ranges of $-\infty \sim -u_2$ and $u_2 \sim \infty$ $$E = \int_{-\infty}^{-u_2} P(u - u',\theta)\phi(u') du' + \int_{u_2}^{\infty} P(u - u',\theta)\phi(u') du' \quad (5)$$

is not zero and the distribution f(x, y) encounters the influence of E≠0. By using the above assumption, i.e. the relation of $P(u, \theta) = P_o$ at the range except $u = o \sim u_2$, however, the equation (5) can be represented as follows:

$$E = P_o \int_{-\infty}^{-u_2} \phi(u') du' + P_o \int_{u_2}^{\infty} \phi(u') du' \quad (6)$$

In the equation (6), the integration E has no relation to P(u, θ). Therefore, if $$\int_{-\infty}^{-u_2} \phi(u') du' \text{ and } \int_{u_2}^{\infty} \phi(u') du'$$

are beforehand or previously evaluated, a convolution integration over an infinite region can be substantially realized.

Figure 4A:
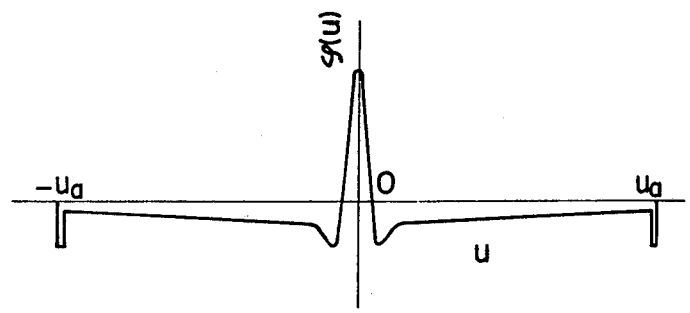
FIGS. 4A to 4C are views for explaining the principle of this invention.

FIG. 4A shows the shape of a weighting function used in this invention. The values of the weighting function φ(u) of FIG. 4A at $u = u_a$ or $u = -u_a$ can be given by means of the equation (6) as follows:

$$\begin{aligned} \phi(u_a) &= \phi(-u_a) \\ &= \int_{-u_a}^{-\infty} \phi(u) du \\ &= \int_{u_a}^{\infty} \phi(u) du \end{aligned} \quad (7)$$

Figure 4B:
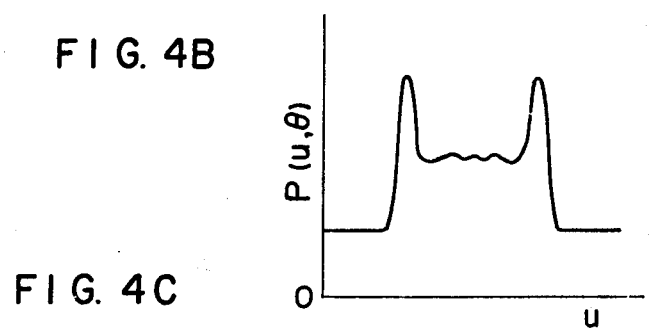
Figure 4C:
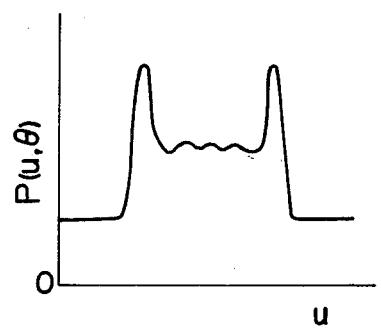

How to select $u_a$ will now be explained. The convolution integration operation starts when P(u, θ) and φ(u) have a positional relationship as shown in FIGS. 4A and 4B. The sum of the products of p(u, θ) and φ(u) is made until P(u, θ) and φ(u) reach a positional relationship as shown in FIGS. 4A and 4B. Therefore, it is enough to select the position of φ($u_a$) at or outside one end of P(u, θ) even if φ(o) or the zero order of φ(u) is located corresponding to whichever position of P(u, θ). Assuming that P(u, θ) has been sampled at M points, it is enough if the weighting function φ(u) has at least (2M−1) known weight values. If the first and last weight values of the weighting function φ(u), i.e. φ($u_a$) and φ($-u_a$), are selected to be the values defined by the equation (7), an integration over an infinite region be substantially realized by an integration over a finite region.

Though an accurately reconstructed distribution of absorption or transmittance of radiation by or through a cross-section of an object under consideration can be obtained in accordance with the first aspect of this invention using the weighting function shown in FIG. 4A, the multiplication operation of total (2M−1) times with respect to (2M−1) weight values of φ(u) must be carried out for each value of P(u, θ) sampled by M points, thereby requiring a long processing time. Furthermore, since only M values of P(u, θ) exist, (M−1) ones among (2M−1) arithmetic-operations are the multiplication of φ(u) with a constant value ($P_o$).

In accordance with a second aspect of this invention, the total number of arithmetic operations can be reduced from 2M−1 to M+2, as explained hereinunder. Assuming that data is sampled at M points and that P(u, θ) and φ(u) are represented by P(m, θ) and φ(n), m being $m = 0 \sim (m - 1)$ and $n = (-M + 1) \sim (M - 1)$, the equation (2) may be replaced in a discrete form as follows:

$$f(x,y) = \sum_\theta \sum_{n=-\infty}^{\infty} P(m + n,\theta) \phi(n) \quad (8)$$

If the relation $$m + n < 0 \text{ or } m + n > M - 1 \quad (9)$$

is satisfied, P(m+n, θ) does not exist and hence a constant value $P_o$ is used. Thus, the equation (8) may be transformed into the following equation:

$$\begin{aligned} f(x,y) = \sum_\theta \bigg\{ &\sum_{n=N_1}^{N_2} P(m + n,\theta) \phi(n) \\ &+ P_o \sum_{n=-\infty}^{N_1-1} \phi(n) + P_o \sum_{n=N_2+1}^{\infty} \phi(n) \bigg\} \\ &(N_1 = -m, N_2 = M - m) \end{aligned} \quad (10)$$

The second and third terms of the equation (10) can be determined irrespective of P(m, θ). Therefore, if the values $$\psi_1(n) = \sum_{i=-\infty}^{-n-1} \phi(i)$$
$$\psi_2(n) = \sum_{i=M+n}^{\infty} \phi(i)$$
(11)

are beforehand or previously evaluated, it is possible to realize the arithmetic operation of the equation (10) with finite times as shown by the following equation (12):

$$f(x,y) = \sum_{\theta} \left( \sum_{n=N_1}^{N_2} P(m+n,\theta)\phi_n + P_o\psi_1(N_1-1) + P_o\psi_2(N_2+1) \right)$$
(12)

The multiplication operation for the first term of the equation (12) is carried out $(N_2 - N_1 =)$ M times and the calculation of the equation (12) is achieved by the multiplication operation of total $(M+2)$ times. For example, when $M=256$ is employed, an integration over an infinite region can be substantially realized by the multiplication operation of 258 times though the first aspect of this invention requires the multiplication operation of $(2M-1=) 511$ times.

Figure 5:
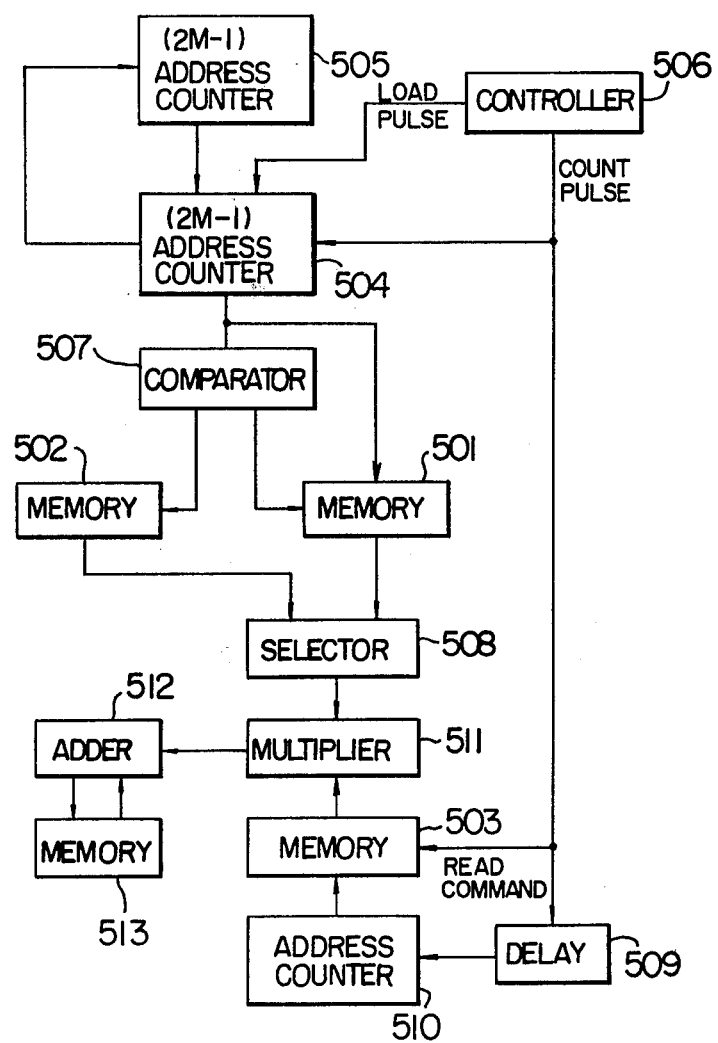
FIG. 5 shows a circuit diagram of an image reconstructing section of the tomographic imaging system according to one embodiment of this invention.

FIG. 5 shows a circuit diagram of an image reconstructing section of the tomographic imaging system for performing the first aspect of this invention. The shown embodiment will be explained with respect to the case where an weighting function has $(2M-1)$ known weight values for M sampled data.

In FIG. 5, detected data P(u, θ), a constant value $P_o$ and an weighting function $\phi(u)$ are stored in memories 501, 502 and 503 respectively. Reference numerals 504 and 505 represent scale-of-$(2M-1)$ counters and the initial contents of the counter 505 are set to be zero. A controller circuit 506 supplies a load pulse to the counter 504 to receive the contents of the counter 505 and subsequently supplies a count pulse to the counter 504. A comparator circuit 507 for checking the contents of the counter 504 to determine whether detected data exist at an address of the memory 501 designated by the counter 504 or not, causes the memory 501 to deliver its contents to a selector circuit 508 when the detected data exist at that address and causes the memory 502 to deliver its contents to the selector circuit 508 when no detected data exist.

The count pulse from the controller circuit 506 also serves as a read command to the memory 503 (in which the weighting function $\phi(u)$ is stored) and is applied through a delay circuit 509 to an address counter 510. The contents of the address counter 510 are previously cleared to be zero.

A multiplier circuit 511 performs the multiplication of the detected data sent from the selector circuit 508 and the value of the weighting function at an address of the memory 503 designated by the counter 510. An adder circuit 512 produces the sum of the contents of a memory 513 (whose initial contents are zero) and the results of the multiplication operation of the multiplier circuit 511. The results of the sum operation in the adder circuit 512 are stored in the memory 513.

After the above procedure has been carried out $(2M-1)$ times in conjunction with $(2M-1)$ values of the weighting function, a carry pulse is applied from the memory 504 to the memory 505 so that the contents of the memory 505 are advanced by unit. On the other hand, the contents of the counter 510 are reset to be zero. A sequence of the above procedures are carried out until the contents of the memory 505 reach M. When the equation (7) is used in the present embodiment, an integration over an infinite region can be thus realized by an integration over a finite region.

Figure 6:
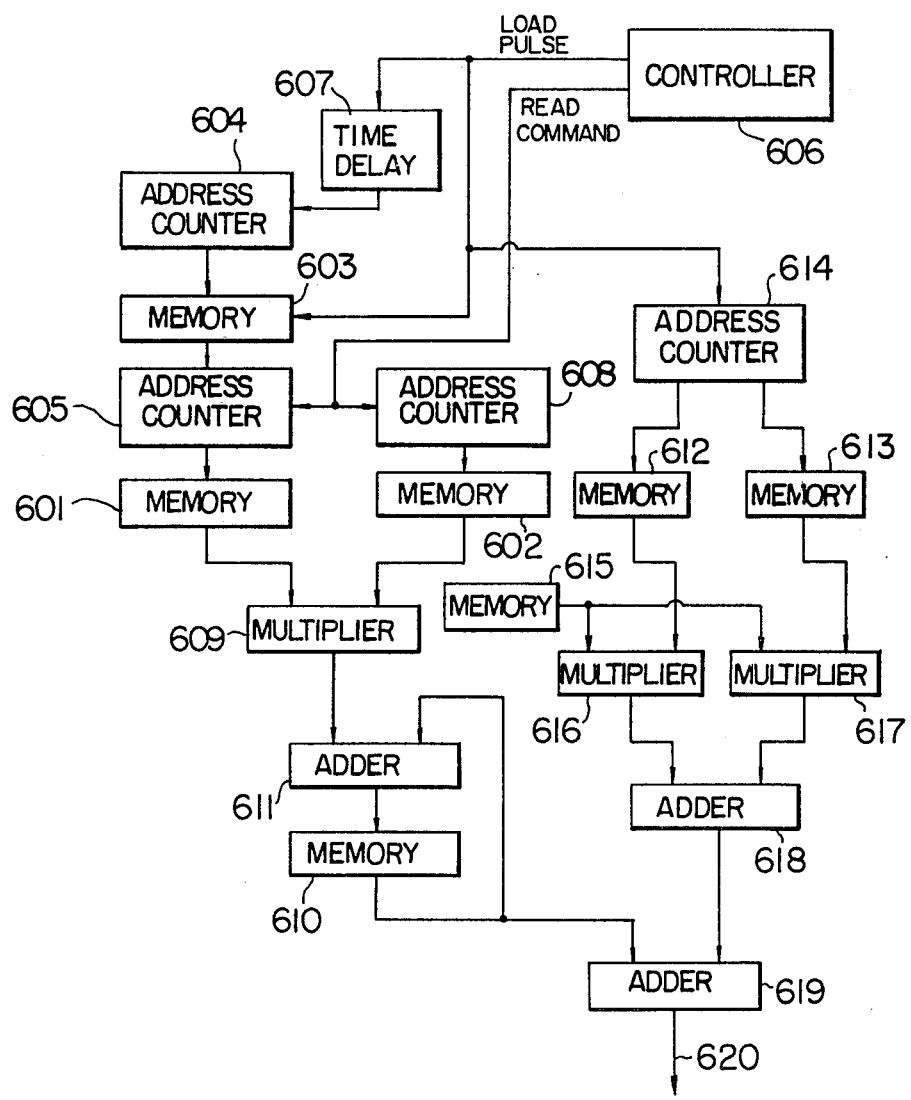
FIG. 6 shows a circuit diagram of an image reconstructing section of the tomographic imaging system according to another embodiment of this invention.

FIG. 6 shows a circuit diagram of an image reconstruction section of the tomographic imaging system for performing the second aspect of this invention, in which the number of multiplication operations is reduced.

In FIG. 6, $\phi(n)$ and P(m, θ) shown in the equation (10) are stored in memories 601 and 602 respectively. The value of $N_1$ shown in the equation (10) is stored as a function of m in a memory 603. Reference numerals 604, 605 and 608 represent address counters. The initial contents of the counters 604 and 608 are cleared to be zero. A controller circuit 606 supplies a load pulse to the memory 603 to cause its contents to load to the counter 605 from an address of the memory 603 designated by the counter 604. The load pulse from the controller circuit 606 is also applied to the counter 604 through a time delay circuit 607 so that the contents of the counter 604 are advanced by unit after a constant time delay determined by the circuit 604. The controller circuit 606 also supplies a read command or count pulse to the counters 605 and 608 so that the contents of the memories 601 and 602 are sequentially read out at their addresses designated by the counters 605 and 608 and are sent to a multiplier circuit 609. An adder circuit 611 produces the sum of the output from the multiplier circuit 609 and the output from a memory 610 whose initial contents are zero. The results of the sum operation in the adder circuit 611 are stored in the memory 610. By carrying out the above procedure M times, the convolution operation in the first term of the equation (10) would be performed.

Functions of $$\sum_{n=-\infty}^{N_1-1} \phi(n) \text{ and } \sum_{n=N_2+1}^{\infty} \phi(n)$$

shown in the equation (10) are stored in memories 612 and 613 respectively. The contents of an address counter 614 are initially set to be zero and are then advanced by unit in response to the load pulse from the controll circuit 606. A memory 615 stores a constant value $P_o$ appearing in the equation (10). The contents of the memories 612 and 613 are read out at their addresses designated by the contents of the counter 614. The contents read from the memories 612 and 613 are multiplied with the contents $P_o$ of the memory 615 by multiplier circuits 616 and 617 respectively. The outputs from the multiplier circuits 616 and 617 are summed in an adder circuit 618. This procedure is carried out only once during the above-described convolution operation in which the sum of multiplications or products is produced in M times.

After the convolution operation has been completed, the output of the memory 610 and the output of the adder circuit 618 are summed in an adder circuit 619 which in turn produces an output signal 620 representative of the results of arithmetic operation on a part { } of the right side of the equation (10). By repeating this processing with respect to $\theta$ and making back projection by use of the signal 620, a tomographic image of an object under consideration can be produced.

In the foregoing embodiments, the system has been constructed by hard-ware elements. But, it should be understood that a part or the entire of the system can be replaced by computer program.

As described above, a convolution integration operation over an infinite region can be substantially realized by an arithmetic operation of finite times and the quality of reproduced image can be improved, in accordance with this invention.

What is claimed is:

1. A tomographic imaging system comprising:
   irradiating means for irradiating a cross-section of an object under consideration with radiation rays from plural directions;
   detector means for detecting the radiation rays transmitted through the cross-section of said object to produce an output signal;
   first memory means for storing the output signal of said detector means; and
   an image reconstructing section for performing a convolution integral operation on the contents of said first memory means by means of a first weighting function to reconstruct a three-dimensional image of the cross-section of said object, said image reconstructing section including (i) second memory means for storing a second weighting function, said second weighting function being provided with a predetermined positive and negative $(N-1)$th order when the output signal of said detector means produced by the irradiation of the cross-section of said object from one of said plural directions is sampled by N points, the value of the $(N-1)$th order of said second weighting function being an integration of said first weighting function from the $(N-1)$th order to positive infinity and the value of $-(N-1)$th order of said second weighting function being an integration of said first weighting function from the $-(N-1)$th order to negative infinity, (ii) control means for successively reading out the contents of said first and second memory means, and (iii) operational means for performing multiplying and summing operations on the read-out contents of said first and second memory means, said operational means producing the product of the values of the $(N-1)$th and $-(N-1)$th orders of said second weighting function and a component of the output signal of said detector means relating to the radiation rays free from the absorption thereof by said object.

2. A tomographic imaging system according to claim 1, wherein said predetermined positive and negative orders of second weighting function are positioned opposite ends thereof respectively.

3. A tomographic imaging system comprising:
   irradiating means for irradiating a cross-section of an object under consideration with radiation rays from plural directions;
   detector means for detecting the radiation rays transmitted through the cross-section of said object to produce an output signal; and
   an image reconstructing section for performing a convolution integral operation on the output signal of said detector means by means of a predetermined weighting function to reconstruct a three-dimensional image of the cross-section of said object, said image reconstruction section including a first means for generating a first weighting function, a second means for generating second and third weighting functions, said second function being integrations of said first weighting function from predetermined positive orders of said first weighting function to positive infinity and said third weighting function being integrations of said first weighting function from predetermined negative orders of said first weighting function to negative infinity, a third means for producing the product of the output from said detector means and the output from said first means, a fourth means for producing the sum of the outputs from said third means, fifth and sixth means for producing the product of the output from said detector means and said second weighting function and the product of the output from said detector means and said third weighting function, a seventh means for producing the sum of the output from said fifth means and the output from said sixth means, and an eighth means for producing the sum of the output from said fourth means and the output from said seventh means.

* * * * *